(12) United States Patent
Mathijssen et al.

(10) Patent No.: US 10,379,448 B2
(45) Date of Patent: Aug. 13, 2019

(54) METHODS AND APPARATUS FOR PREDICTING PERFORMANCE OF A MEASUREMENT METHOD, MEASUREMENT METHOD AND APPARATUS

(71) Applicant: ASML Netherlands B.V., Veldhoven (NL)

(72) Inventors: Simon Gijsbert Josephus Mathijssen, Rosmalen (NL); Sander Bas Roobol, Veldhoven (NL); Nan Lin, Eindhoven (NL); Willem Marie Julia Marcel Coene, Geldrop (NL); Arie Jeffrey Den Boef, Waalre (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/875,156

(22) Filed: Jan. 19, 2018

(65) Prior Publication Data
US 2018/0224753 A1   Aug. 9, 2018

(30) Foreign Application Priority Data
Feb. 9, 2017 (EP) .................................... 17155453

(51) Int. Cl.
*G03B 27/42* (2006.01)
*G03F 7/20* (2006.01)
(Continued)

(52) U.S. Cl.
CPC ........ *G03F 7/70633* (2013.01); *G01B 11/272* (2013.01); *G01N 21/4788* (2013.01);
(Continued)

(58) Field of Classification Search
CPC ............. G03F 7/70525; G03F 7/70625; G03F 7/70633; G03F 7/7085; G03F 9/7069;
(Continued)

(56) References Cited

U.S. PATENT DOCUMENTS 6,982,793 B1   1/2006   Yang et al.
7,072,442 B1   7/2006   Janik
(Continued)

FOREIGN PATENT DOCUMENTS

EP   0818814 A2   1/1998
EP   3321739 A1   5/2018
(Continued)

OTHER PUBLICATIONS

Yeh et al., "Development of EUV scatterometer with high-harmonic-generation EUV source for nano-scale grating measurement," Nanoengineering: Fabrication, Properties, Optics, and Devices XII, Proc. of SPIE, vol. 9556, 2015; pp. 95561E1-1-95561F1-8.
(Continued)

*Primary Examiner* — Peter B Kim
(74) *Attorney, Agent, or Firm* — Sterne, Kessler, Goldstein & Fox P.L.L.C.

(57) ABSTRACT

Target structures such as overlay gratings (Ta and Tb) are formed on a substrate (W) by a lithographic process. The first target is illuminated with a spot of first radiation (456*a*, Sa) and simultaneously the second target is illuminated with a spot of second radiation (456*b*, Sb). A sensor (418) detects at different locations, portions (460*x*−, 460*x*+) of said first radiation that have been diffracted in a first direction by features of the first target and portions (460*y*−, 460*y*+) of said second radiation that have been diffracted in a second direction by features of the second target. Asymmetry in X and Y directions can be detected simultaneously, reducing the time required for overlay measurements in X and Y. The two spots of radiation at soft x-ray wavelength can be generated simply by exciting two locations (710*a*, 710*b*) in a higher harmonic generation (HHG) radiation source or inverse Compton scattering source.

20 Claims, 9 Drawing Sheets

(51) Int. Cl.
*G01B 11/27* (2006.01)
*G01N 21/47* (2006.01)
*G01N 21/956* (2006.01)
*G03F 9/00* (2006.01)

(52) U.S. Cl.
CPC ......... *G01N 21/956* (2013.01); *G03F 7/7085* (2013.01); *G03F 7/70525* (2013.01); *G03F 7/70625* (2013.01); *G03F 9/7069* (2013.01); *G03F 9/7088* (2013.01)

(58) Field of Classification Search
CPC . G03F 9/7088; G01B 11/272; G01N 21/4788; G01N 21/956
See application file for complete search history.

(56) References Cited

U.S. PATENT DOCUMENTS

| | | | |
|---|---|---|---|
| 9,823,586 B2 | 11/2017 | Quintanilha | |
| 2006/0033921 A1 | 2/2006 | Den Boef et al. | |
| 2006/0066855 A1 | 3/2006 | Boef et al. | |
| 2008/0239318 A1 | 10/2008 | Den Boef et al. | |
| 2010/0201963 A1 | 8/2010 | Cramer et al. | |
| 2011/0069292 A1 | 3/2011 | Den Boef | |
| 2011/0292365 A1 | 12/2011 | Cramer et al. | |
| 2012/0242970 A1 | 9/2012 | Smilde et al. | |
| 2014/0192338 A1 | 7/2014 | Den Boef | |
| 2016/0282282 A1 | 9/2016 | Quintanilha et al. | |
| 2017/0184511 A1 | 6/2017 | Den Boef et al. | |
| 2018/0136568 A1 | 5/2018 | Roobol et al. | |
| 2018/0160520 A1 | 6/2018 | Van Heumen | |

FOREIGN PATENT DOCUMENTS

| | | |
|---|---|---|
| TW | 201523169 A | 6/2015 |
| WO | WO 2015/172963 A1 | 11/2015 |
| WO | WO 2017/025373 A1 | 2/2017 |
| WO | WO 2017/025392 A1 | 2/2017 |
| WO | WO 2017/108404 A1 | 6/2017 |
| WO | WO 2017/108410 A1 | 6/2017 |
| WO | WO 2018/086816 A2 | 5/2018 |

OTHER PUBLICATIONS

International Search Report and Written Opinion of the International Searching Authority directed to related International Patent Application No. PCT/EP2018/050382, dated May 18, 2018; 10 pages.

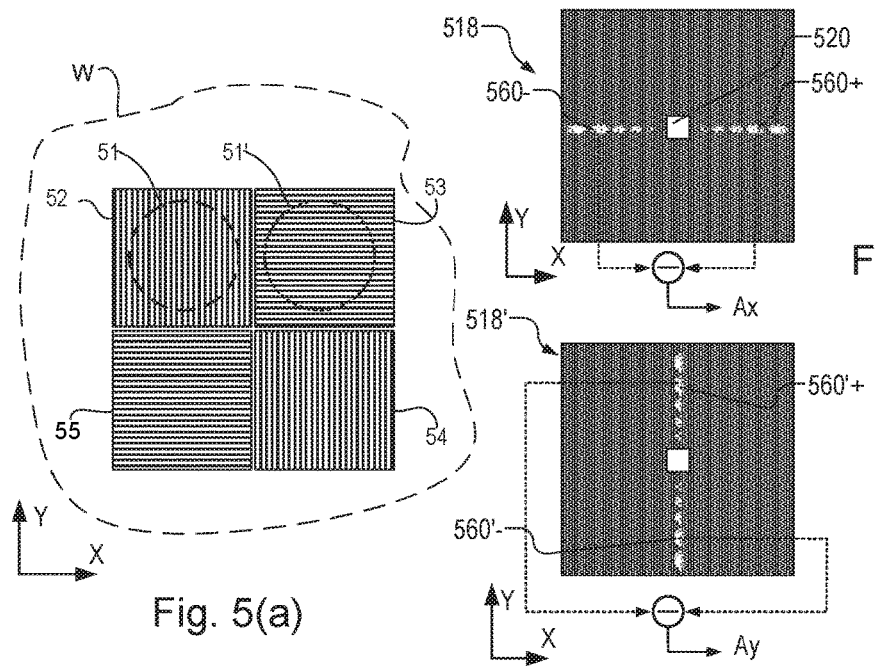
Fig. 5(a)
Fig. 5(b)
Fig. 5(c)
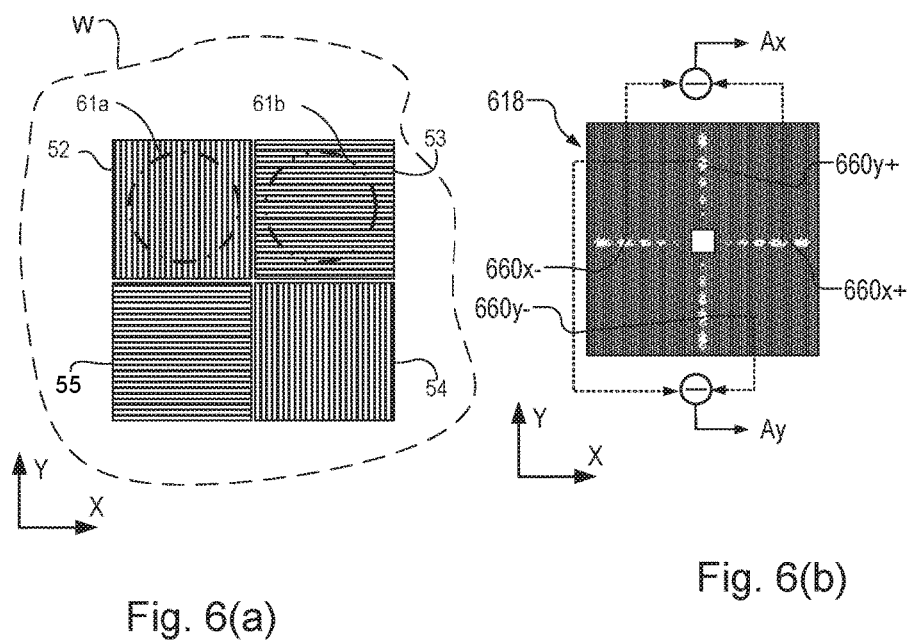
Fig. 6(a)
Fig. 6(b)

METHODS AND APPARATUS FOR PREDICTING PERFORMANCE OF A MEASUREMENT METHOD, MEASUREMENT METHOD AND APPARATUS

FIELD

The present disclosure relates to methods and apparatus for inspection (e.g., metrology) usable, for example, in the manufacture of devices by lithographic techniques and to methods of manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. These target portions are commonly referred to as "fields."

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a diffraction "spectrum" from which a property of interest of the target can be determined.

Examples of known scatterometers include angle-resolved scatterometers of the type described in US2006033921A1 and US2010201963A1. The targets used by such scatterometers are relatively large, e.g., 40 µm by 40 µm, gratings and the measurement beam generates a spot that is smaller than the grating (i.e., the grating is underfilled). In addition to measurement of feature shapes by reconstruction, diffraction based overlay can be measured using such apparatus, as described in published patent application US2006066855A1. An overlay measurement is typically obtained by measuring asymmetry of two overlay gratings, each having a different programmed (deliberate) offset or "bias." Diffraction-based overlay metrology using dark-field imaging of the diffraction orders enables overlay measurements on smaller targets. Examples of dark field imaging metrology can be found in published patent applications US2014192338 and US2011069292A1. Further developments of the technique have been described in several published patent publications. These targets can be smaller than the illumination spot and may be surrounded by product structures on a wafer. Multiple gratings can be measured in one image, using a composite grating target. These developments have allowed the overlay measurements that are fast and computationally very simple (once calibrated).

At the same time, the known dark-field imaging techniques employ radiation in the visible or ultraviolet waveband. This limits the smallest features that can be measured, so that the technique can no longer measure directly the smallest features made in modern lithographic processes. To allow measurement of smaller structures, it has been proposed to use radiation of shorter wavelengths, similar for example to the extreme ultraviolet (EUV) wavelengths used in EUV lithography. Such wavelengths may also be referred to as soft x-ray wavelengths and may be in the range 1 to 100 nm, for example. Examples of transmissive and reflective metrology techniques using these wavelengths in transmissive and/or reflective scattering modes are disclosed in published patent application WO2015172963A1. Further examples of metrology techniques and apparatuses using these wavelengths in transmissive and/or reflective scattering modes are disclosed in the pending patent applications PCT/EP2016/068317 and U.S. Ser. No. 15/230,937 (claiming priority from EP15180807.8 filed 12 Aug. 2015) and PCT/EP2016/068479 (claiming priority from EP15180740.1 filed 12 Aug. 2015), not published at the present priority date. The contents of all these applications are incorporated herein by reference.

Convenient sources of SXR radiation include higher harmonic generation (HHG) sources, in which infrared pump radiation from a laser is converted to shorter wavelength radiation by interaction with a gaseous medium. HHG sources are available for example from KMLabs, Boulder Colo., USA (http://www.kmlabs.com/). Various modifications of HHG sources are also under consideration for application in inspection apparatus for lithography. Some of these modifications are disclosed for example in European patent application number 16198346.5 dated Nov. 11, 2016, not been published at the priority date of the present application. Other modifications are disclosed in U.S. patent application Ser. No. 15/388,463 and international patent application PCT/EP2016/080103, both claiming priority from European patent application no. 15202301.6 dated Dec. 23, 2015, also not yet been published at the priority date of the present application. The contents of both of these applications are incorporated herein by reference. Another type of source is the inverse Compton scattering (ICS) source, described in application PCT/EP2016/068479, mentioned above No single metrology technique meets all requirements, and hybrid metrology systems have been proposed to combine different types of measurement and different wavelengths in a compact and cost-effective system. Examples of such hybrid techniques are disclosed in international patent application PCT/EP2016/080058, not published at the present priority date.

Unfortunately, the cost and other limitations of optical systems compatible with such wavelengths make it commercially unattractive to implement small-target dark-field imaging.

SUMMARY OF THE INVENTION

The invention aims to improve the throughput of inspection apparatus operating with SXR wavelength radiation, where the speed advantages of dark-field imaging are not available.

The present invention in a first aspect provides an inspection apparatus comprising an illumination system and a detection system,
wherein the illumination system includes a source arrangement for generating first radiation at a first source location in a radiation generation space and for simultaneously generating second radiation at a second source location in the same radiation generation space, the first radiation and the second radiation including wavelengths less than 100 nm,
wherein an optical system of the illumination system is arranged to focus radiation from both the first source location and the second source location so as to illuminate a first target location with a spot of said first radiation while simultaneously illuminating a second target location with a spot of said second radiation, and
wherein the detection system is arranged to detect, at one or more first detection locations, portions of said first radiation that have been diffracted in a first direction by a first target structure at the first target location and simultaneously to detect, at one or more second detection locations, portions of said second radiation that have been diffracted in a second direction by features of a second target structure positioned at the second target location.

In this way, measurements of, for example, measurements asymmetry can be made on two targets simultaneously, even without the facility of dark-field imaging. The measurement of two targets simultaneously greatly reduces the measurement overhead required to measure a number of targets in different directions.

The present invention in a second aspect provides a method of inspecting structures that have been formed on a substrate by a lithographic process, the method comprising:
illuminating a first target with first radiation and simultaneously illuminating a second target with second radiation, the first radiation and the second radiation including wavelengths less than 100 nm;
detecting, at one or more first detection locations, portions of said first radiation that have been diffracted in a first direction by features of the first target; and
detecting, at one or more second detection locations, portions of said second radiation that have been diffracted in a second direction by features of the second target.

The method can be performed for example using the inspection apparatus of the first aspect of the invention as set forth above. In a simpler implementation, the method can also be performed using a single spot of radiation which extends partly over the first target and partly over the second target.

The invention further provides a manufacturing devices, the method including a lithographic process step, wherein, before or after performing said lithographic process step, measurements are obtained of first and second targets on a substrate by a method according to the second aspect of the invention as set forth above, and wherein the obtained measurements are used to adjust parameters of the lithographic process step for the processing of the substrate and/or further substrates.

The invention further provides a computer program product comprising machine-readable instructions for causing a processor to implement the processing arrangement of an inspection apparatus according to the first aspect of the invention, as set forth above. The machine-readable instructions may be provided in a non-transitory storage medium.

The invention further provides a system comprising an inspection apparatus configured to provide a beam of radiation on a target structure, and to detect radiation diffracted by the targets to determine a parameter of a patterning process, in combination with the computer program according to the invention as set forth above. The system may further comprise a lithographic apparatus comprising a support structure configured to hold a patterning device to modulate a radiation beam and a projection optical system arranged to project the modulated radiation beam onto a radiation-sensitive substrate.

Further features and advantages, as well as the structure and operation of various embodiments, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments will now be described, by way of example only, with reference to the accompanying drawings in which:

FIGS. 5(a)-5(c) show 5(a) a composite grating target and 5(b)-5(c) detected diffraction signals in the inspection apparatuses of FIGS. 3 and 4, without using the present invention;

FIGS. 6(a)-6(b) show 6(a) a composite grating target and 6(b) detected diffraction signals in the inspection apparatuses of FIGS. 3 and 4, when the present invention is applied;

DETAILED DESCRIPTION OF EXEMPLARY EMBODIMENTS

Before describing embodiments of the invention in detail, it is instructive to present an example environment in which embodiments of the present invention may be implemented.

Figure 1:
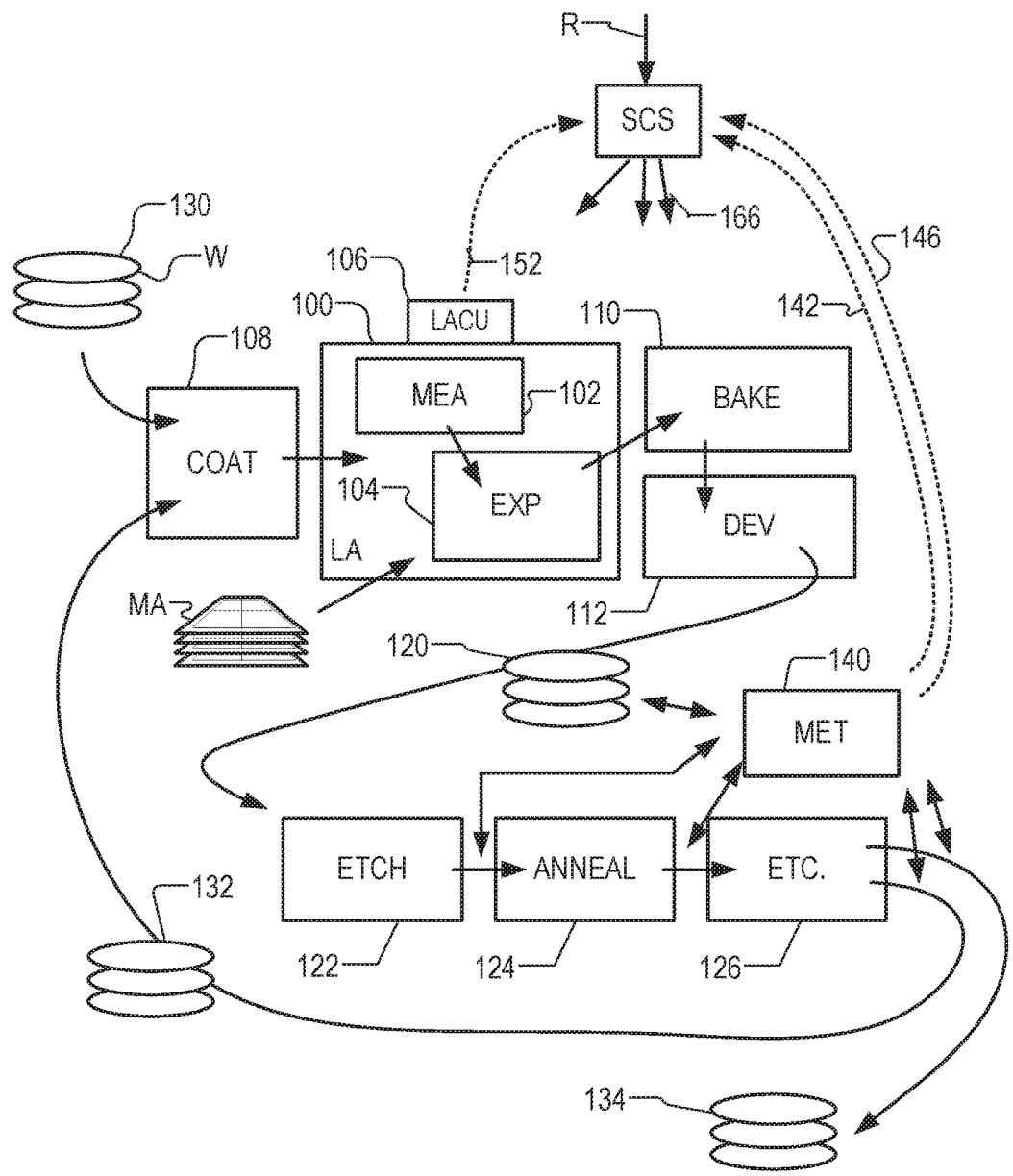
FIG. 1 depicts a lithographic apparatus together with other apparatuses forming a production facility for semiconductor devices, and including a hybrid metrology apparatus including an inspection apparatus according to an embodiment of the present invention.

FIG. 1 at 100 shows a lithographic apparatus LA as part of an industrial facility implementing a high-volume, lithographic manufacturing process. In the present example, the manufacturing process is adapted for the manufacture of for semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 100 for short), a measurement station MEA is shown at 102 and an exposure station EXP is shown at 104. A control unit LACU is shown at 106. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation, for example, may include electromagnetic radiation in the deep ultraviolet (DUV) or extreme ultraviolet (EUV) wavebands. The present disclosure is also applicable to other types of lithographic process, for example, imprint lithography and direct writing lithography, for example by an electron beam.

The lithographic apparatus control unit LACU controls all the movements and measurements of various actuators and sensors, causing the apparatus to receive substrates W and reticles MA and to implement the patterning operations. LACU also includes signal processing and data processing capacity to implement desired calculations relevant to the operation of the apparatus. In practice, control unit LACU will be realized as a system of many sub-units, each handling the real-time data acquisition, processing, and control of a subsystem or component within the apparatus.

Before the pattern is applied to a substrate at the exposure station EXP, the substrate is processed in at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of many marks across the substrate area, if the apparatus is to print product features at the correct locations with very high accuracy.

The lithographic apparatus LA may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming, and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. When lithographic apparatus LA is of a so-called dual stage type which has two substrate tables, the exposure station and the measurement station may be distinct locations between which the substrate tables can be exchanged. [This is only one possible arrangement, however, and the measurement station and exposure station need not be so distinct. For example, it is known to have a single substrate table, to which a measurement stage is temporarily coupled during the pre-exposure measuring phase. The present disclosure is not limited to either type of system.]

Within the production facility, apparatus 100 forms part of a "litho cell" or "litho cluster" that also contains a coating apparatus 108 for applying photosensitive resist and other coatings to substrates W for patterning by the apparatus 100. At an output side of apparatus 100, a baking apparatus 110 and developing apparatus 112 are provided for developing the exposed pattern into a physical resist pattern. Between all of these apparatuses, substrate handling systems take care of supporting the substrates and transferring them from one piece of apparatus to the next. These apparatuses, which are often collectively referred to as the "track," are under the control of a track control unit which is itself controlled by a supervisory control system SCS, which also controls the lithographic apparatus via lithographic apparatus control unit LACU. Thus, the different apparatuses can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 120 are transferred to other processing apparatuses such as are illustrated at 122, 124, and 126. A wide range of processing steps is implemented by various apparatuses in a typical manufacturing facility. For the sake of example, apparatus 122 in this embodiment is an etching station, and apparatus 124 performs a post-etch annealing step. Further physical and/or chemical processing steps are applied in further apparatuses, 126, etc. Numerous types of operation can be required to make a real device, such as deposition of material, modification of surface material characteristics (oxidation, doping, ion implantation, etc.), chemical-mechanical polishing (CMP), and so forth.

The apparatus 126 may, in practice, represent a series of different processing steps performed in one or more apparatuses.

As is well known, the manufacture of semiconductor devices involves many repetitions of such processing, to build up device structures with appropriate materials and patterns, layer-by-layer on the substrate. Accordingly, substrates 130 arriving at the litho cluster may be newly prepared substrates, or they may be substrates that have been processed previously in this cluster or in another apparatus entirely. Similarly, depending on the required processing, substrates 132 on leaving apparatus 126 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 126 used at each layer may be completely different in type. Further, even where the processing steps to be applied by the apparatus 126 are nominally the same, in a large facility, there may be several supposedly identical machines working in parallel to perform the step 126 on different substrates. Small differences in set-up or faults between these machines can mean that they influence different substrates in different ways. Even steps that are relatively common to each layer, such as etching (apparatus 122) may be implemented by several etching apparatuses that are nominally identical but working in parallel to maximize throughput. In practice, moreover, different layers require different etch processes, for example, chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly, a manufacturing facility in which litho cell LC is located also includes metrology system MET which receives some or all of the substrates W that have been processed in the litho cell. Metrology results are provided directly or indirectly to the supervisory control system (SCS) 138. If errors are detected, adjustments may be made to exposures of subsequent substrates, especially if the metrology can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Also shown in FIG. 1 is a metrology apparatus 140 which is provided for making measurements of parameters of the products at desired stages in the manufacturing process. A common example of a metrology apparatus in a modern lithographic production facility is a scatterometer, for example, an angle-resolved scatterometer or a spectroscopic scatterometer, and it may be applied to measure properties of the developed substrates at 120 prior to etching in the apparatus 122. Using metrology apparatus 140, it may be determined, for example, that important performance parameters such as overlay or critical dimension (CD) do not meet specified accuracy requirements in the developed resist. Prior to the etching step, the opportunity exists to strip the developed resist and reprocess the substrates 120 through the litho cluster. As is also well known, the metrology results 142 from the apparatus 140 can be used to maintain accurate performance of the patterning operations in the litho cluster, by supervisory control system SCS and/or control unit LACU 106 making small adjustments over time, thereby minimizing the risk of products being made out-of-specification, and requiring re-work. Of course, metrology apparatus 140 and/or other metrology apparatuses (not shown) can be applied to measure properties of the processed substrates 132, 134, and incoming substrates 130.

Metrology apparatus 140 may if desired implement a hybrid metrology system. A common example of a metrology apparatus in a modern lithographic production facility is a scatterometer, for example, an angle-resolved scatterometer or a spectroscopic scatterometer, and it may be applied to measure properties of the developed substrates at 120 prior to etching in the apparatus 122. A hybrid metrology system may include scatterometers working at different wavelengths, and additional types of inspection apparatus, so that multiple types of measurement can be performed within the hybrid metrology system to obtain a better overall measurement of a parameter or parameters of interest on a given target structure.

Each of the inspection apparatuses within a hybrid metrology system can have a particular illumination system for radiation of a particular characteristic. More detailed examples of the types of apparatuses that can be combined are given in the pending international patent application number PCT/EP2016/080058, mentioned above. The present disclosure concerns a particular form of inspection apparatus and method, which can be applied as one of the inspection apparatuses in a hybrid metrology system, but can also be applied independently, if desired.

Each generation of lithographic manufacturing technology (commonly referred to as a technology "node") has tighter specifications for performance parameters such as CD. One of the main challenges in metrology is that the size of features within the product and becomes smaller and smaller, and this smaller feature size should also be reflected in the design of metrology targets. Accordingly, metrology apparatus 140 may include an inspection apparatus designed to operate with radiation at wavelengths shorter than conventional visible or UV wavelengths. As a particular example, soft x-ray (SXR) radiation (also called extreme ultraviolet EUV radiation) radiation may be used, with wavelengths in the range 1-100 nm.

Figure 2A:
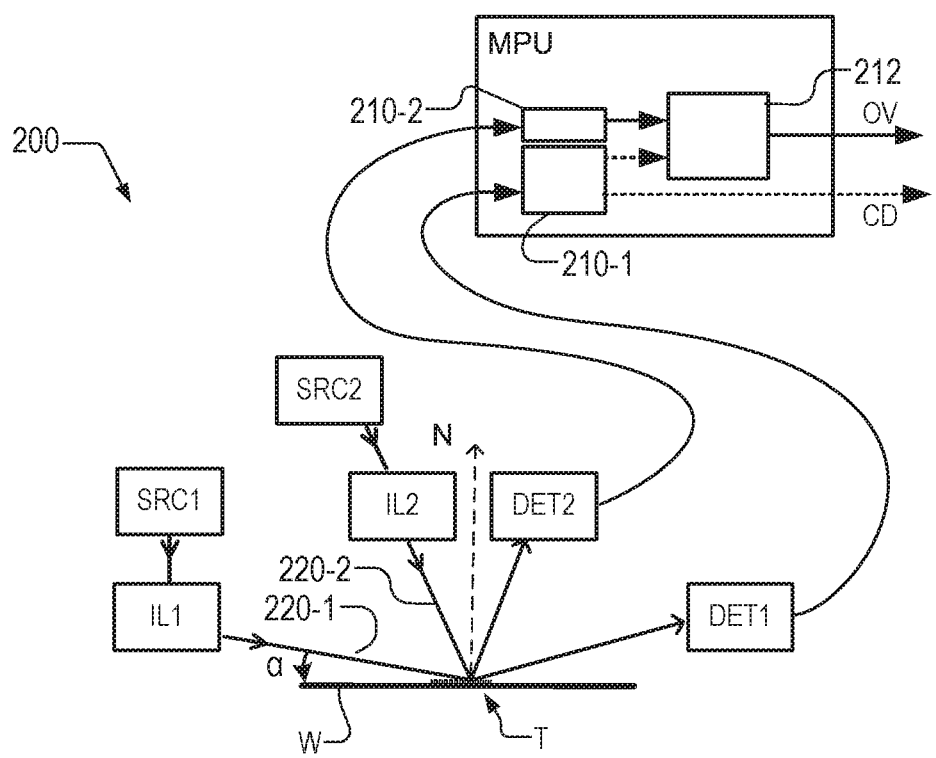
FIGS. 2(a)-2(b) show 2(a) a schematic general arrangement of metrology apparatuses and data flow in an example hybrid metrology apparatus in the production facility shown in FIGS. 1 and 2(b) interaction of grazing incidence radiation and normal incidence radiation with an overlay target structure in the example apparatus.

FIG. 2 illustrates a simple example of a hybrid metrology system 200 in which first and second inspection apparatuses are provided. Each inspection apparatus comprises a radiation source SRC1/SRC2, an illumination system IL1/IL2 and a detection system DET1/DET2/3. A hybrid metrology apparatus can be produced which includes both SXR inspection apparatus for performing measurements at EUV wavelengths and longer-wavelength optical inspection apparatus for performing more conventional measurements. In other examples, both the first and second inspection apparatuses may be designed to operate with SXR radiation, of the same or different wavelengths. Both inspection apparatuses may work simultaneously on the same parts or different parts of the same substrate W. The two inspection apparatuses may in practice operate at different times, while sharing common components such as substrate handling and positioning systems. The metrology apparatuses may be integrated with either the lithographic apparatus LA itself or within the lithographic cell LC. Within a metrology processing unit MPU, dedicated modules 210-1, 210-2 may be are provided to process to some extent data received from each of the detection systems DET1/DET2. Pre-processed results are delivered from these dedicated modules to a hybrid processing module 212, which combines information from the individual inspection apparatus to obtain the measurement of the desired parameter of target structure T.

Figure 2B:
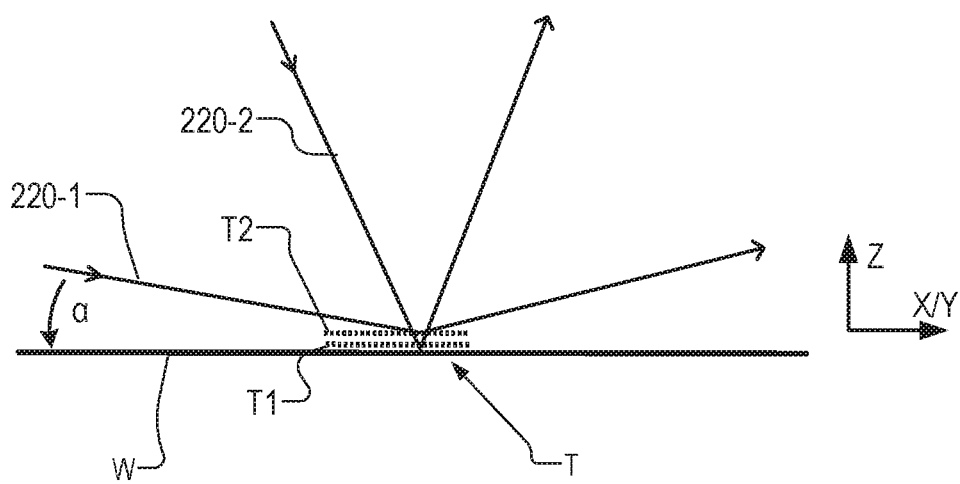

In the particular example of FIG. 2, it is desired to measure a property related to asymmetry of the target structure, for example to obtain a measure of overlay as a performance parameter of the lithographic process. As shown in FIG. 2(b), target structure T may comprise grating features T1 in a lower layer, and T2 in an upper layer. Either or both of these structures may be buried beneath further layers, not shown. When measuring overlay, the reported measurement known methods can be very sensitive to asymmetry not caused by overlay as such. Application of hybrid metrology techniques using the system of FIG. 2 can help to isolate those effects which are truly due to the parameter of interest from those having other causes.

One way in which accuracy of an overlay measurement can be improved can be seen in the enlarged schematic detail of FIG. 2 (b). First radiation 220-1 used in a first inspection step has grazing incidence and penetrates very little into a stack of layers formed on substrate W. First spectrum data is captured by first detection system DET1 with little influence from the lower layers. Properties of the upper layer containing grating features T2 can then be measured and reported by dedicated module 210-1. Second radiation 220-2 having a higher angle of incidence, and possibly having different wavelength characteristics and other properties, penetrates more fully into the stack. Consequently, second spectrum data contains asymmetry information related to the parameter of interest, specifically asymmetry of the overlay target comprising upper and lower grating features T1 and T2 together. Combining the processing of these spectra in the hybrid processing module 212, the overlay measurement that is carried in the second spectrum can be adjusted to remove the influence of the lower layers, using the knowledge gained from the first spectrum.

Overlay between layers is just one example of an asymmetry-related parameter of a target structure. In a multiple-patterning process, structures are formed in one layer of the product not in one patterning operation but in two or more patterning steps. Thus, for example, a first population of structures may be interleaved with a second population of structures, and the populations are formed in different steps, so as to achieve a higher resolution than one step alone can produce. While the placement of the populations should be identical and perfect in relation to other features on the substrate, of course, every real pattern exhibits a certain positional offset. Any unintentional positional offset between the populations can be regarded as a form of overlay and can be measured by asymmetry of the target grating or product features formed by multiple patterning processes. Other types of asymmetry, for example, sidewall asymmetry and trench bottom asymmetry can also be measured, for a simple grating structure.

Using the hybrid metrology system, crosstalk between these different asymmetry-related parameters of can be reduced, to isolate measurements of a parameter of interest. As mentioned already, the present disclosure is not limited to hybrid metrology systems.

Figure 3:
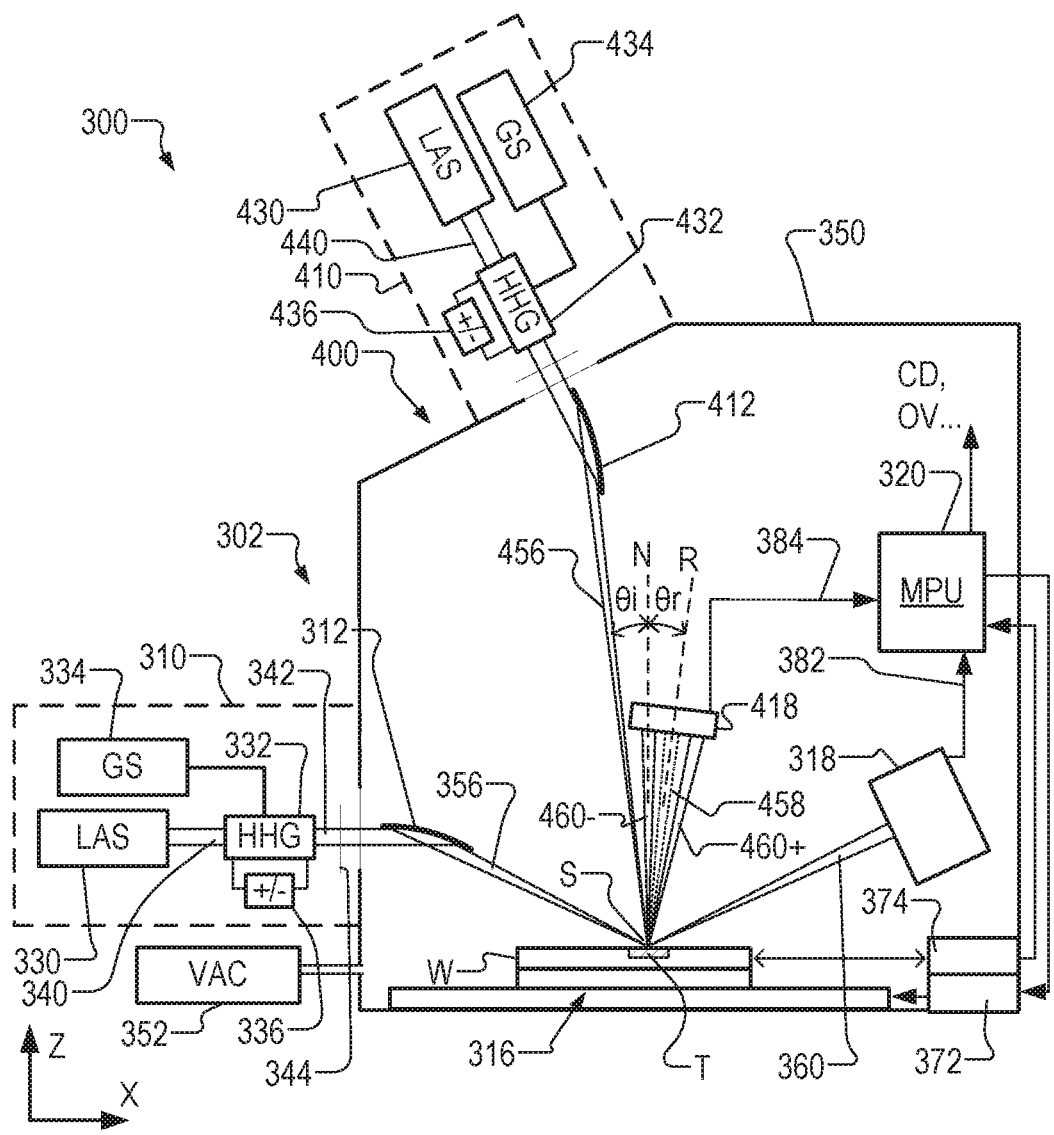
FIG. 3 shows in more detail the arrangement of components in the example hybrid metrology apparatus of FIG. 2, the hybrid metrology apparatus including a first embodiment of an inspection apparatus in which the present invention may be applied.

FIG. 3 illustrates a schematic physical arrangement of hybrid metrology system 300 as an example of the hybrid metrology system 200 of FIG. 2. The hybrid metrology system may be a stand-alone device or incorporated in either the lithographic apparatus LA, or the lithographic cell LC. The apparatus may, of course, be used in conjunction with other apparatuses, such as an SEM apparatus, as part of a larger metrology system.

Hybrid metrology system 300 in this example includes a first inspection apparatus 302 using SXR radiation in grazing incidence, which may be similar to the first inspection apparatus of FIG. 2. A second inspection apparatus 304 is provided in the form of a scatterometer, which uses SXR radiation in normal or near-normal incidence similar to the second inspection apparatus of FIG. 2. First inspection apparatus 302 comprises a first radiation source (SRC1) 310, a first illumination system (IL1) 312, a substrate support 316, a first detection system (DET1) 318, and part of a metrology processing unit (MPU) 320. Source 310 in this example comprises, for example, a generator of EUV or soft x-ray radiation based on high harmonic generation (HHG) techniques. Such sources are available for example from KMLabs, Boulder Colo., USA (http://www.kmlabs.com/). Main components of the radiation source are a pump laser 330 and an HHG gas cell 332. A gas supply 334 supplies suitable gas to the gas cell, where it is optionally ionized by an electric source 336. The pump laser may be for example a fiber-based laser with an optical amplifier, producing pulses of infrared radiation that may last for example less than 1 ns (1 nanosecond) per pulse, with a pulse repetition rate up to several megahertz, as required. The wavelength of the infrared radiation may be for example in the region of 1 μm (1 micron). The laser pulses are delivered as a first radiation beam 340 to the HHG gas cell 332, where the gas a portion of the radiation is converted to higher frequencies the first radiation into a beam 342 including coherent radiation of the desired SXR wavelength or wavelengths.

The radiation may contain multiple wavelengths. If the radiation is also monochromatic, then measurement calculations (for example reconstruction) may be simplified, but it is easier with HHG to produce radiation with several wavelengths. The volume of gas within the gas cell 332 defines an HHG space, although the space need not be completely enclosed and a flow of gas may be used instead of a static volume. The gas may be for example a noble gas such as neon (Ne) or argon (Ar). These are matters of design choice, and may even be selectable options within the same apparatus. Different wavelengths will, for example, provide different levels of contrast when imaging structure of different materials. For inspection of metal structures or silicon structures, for example, different wavelengths may be selected to those used for imaging features of (carbon-based) resist, or for detecting contamination of such different materials. One or more filtering devices 344 may be provided. For example, a filter such as a thin membrane of Aluminum (Al) may serve to cut the fundamental IR radiation from passing further into the inspection apparatus. A grating may be provided to select one or more specific harmonic wavelengths from among those generated in the gas cell. Some or all of the beam path may be contained within a vacuum environment, bearing in mind that SXR radiation is absorbed when traveling in air. The various components of radiation source 310 and illumination optics 312 can be adjustable to implement different metrology 'recipes' within the same apparatus. For example, different wavelengths and/or polarization can be made selectable.

For high-volume manufacturing applications, selection of a suitable source will be guided by cost and hardware size, not only by theoretical ability, and HHG sources are selected as the example here. Other types of sources are also available or under development that may be applied in principle. Examples are synchrotron sources, FEL (free electron laser) sources and so-called x-ray lasers. A source based on inverse Compton scattering could also be used.

Depending on the materials of the structure under inspection, different wavelengths may offer a desired level of penetration into lower layers. For resolving the smallest device features and defects among the smallest device features, then a short wavelength is likely to be preferred. One or more wavelengths in the range 1-20 nm or 1-10 nm may be chosen, for example. Wavelengths shorter than 5 nm suffer from very low critical angle when reflecting off materials typically of interest in semiconductor manufacture. Therefore to choose a wavelength greater than 5 nm will provide stronger signals at higher angles of incidence. On the other hand, if the inspection task is for detecting the presence of a certain material, for example, to detect contamination, then wavelengths up to 50 nm could be useful.

From the first radiation source 310, the filtered beam 342 enters an inspection chamber 350 where the substrate W including a structure of interest is held for inspection by substrate support 316. The structure of interest is labeled T. The atmosphere within inspection chamber 350 is maintained near vacuum by vacuum pump 352, so that EUV radiation can pass without undue attenuation through the atmosphere. The Illumination system 312 has the function of focusing the radiation into a focused beam 356, and may comprise for example a two-dimensionally curved mirror, or a series of one-dimensionally curved mirrors, as described in international application number PCT/EP2016/080058, mentioned above. The focusing is performed to achieve a round or elliptical spot under 10 µm in diameter, when projected onto the structure of interest. Substrate support 316 comprises, for example, an X-Y translation stage and a rotation stage, by which any part of the substrate W can be brought to the focal point of the beam to in a desired orientation. Thus, the radiation spot S is formed on the structure of interest.

Reflected radiation 360 is captured by first detection system 318 and a first spectrum is provided to metrology processing unit 320 for use in calculating a property of the target structure T. The first illumination system 312 and first detection system 318 thus form a first inspection apparatus. This first inspection apparatus may comprise an SXR spectroscopic reflectometer of the kind described in US2016282282A1. Tilting of the substrate in one or more dimensions may also be provided.

To aid the alignment and focusing of the spot S with desired product structures, inspection apparatus 302 may also provide auxiliary optics using auxiliary radiation under control of metrology processor unit 320. Metrology processor unit 320 can also communicate with a position controller 372 which operates the translation stage and rotation stages. Metrology processor unit 320 receives highly accurate feedback on the position and orientation of the substrate, via sensors. Sensors 374 may include interferometers, for example, which can give accuracy in the region of picometers. In the operation of the first inspection apparatus 302, first spectrum data 382 captured by first detection system 318 is delivered to metrology processing unit 320.

A second inspection apparatus 400 within the hybrid metrology system of FIG. 3 includes a second radiation source 410, a second illumination system 412 and a separate detection system 418. These components may, for example, be the same general form as those of the first inspection apparatus 302, with specific differences highlighted below. Thus radiation source 410 comprises the components 430-440 of an HHG radiation source similar to the like-numbered components 330-340 of radiation source 310.

As in the example of FIG. 2, the second inspection apparatus 400 in this example uses SXR radiation at normal incidence or near-normal incidence to perform diffraction-based measurements of asymmetry. According to the principles of the present disclosure asymmetry is measured on more than one target simultaneously. The measurement of asymmetry on a single target will be described first.

The Illumination system 412 focuses SXR radiation from radiation source 410 the function of focusing the radiation into a focused illumination radiation beam 456, and may comprise, for example, a two-dimensionally curved mirror, or a series of one-dimensionally curved mirrors, as described in international application number PCT/EP2016/080058, mentioned above. The focusing is performed to achieve a round or elliptical spot S which may be, for example, less than 10 µm in diameter. In this example of a hybrid metrology system, it will be assumed that components such as the metrology processing unit 320, position controller 272 and sensors 374 are shared between the first and second inspection apparatuses.

To measure asymmetry of the target T illuminated with spot S, second spectrum data 384 captured by second detection system within second inspection apparatus 400 is delivered to metrology processing unit 320 and analyzed to identify asymmetry in a diffraction spectrum The second spectrum data can be used together with the first spectrum data 382 to calculate improved measurements of asymmetry and/or one or more other parameters of interest. As explained in the international application number PCT/EP2016/080058, mentioned above and incorporated herein by reference, the manner of combining the data can vary. For example, based on spectrum data obtained from one of the inspection apparatuses, a metrology recipe of the other inspection apparatus may be adjusted, before a spectrum is captured by that other apparatus. Alternatively or in addition, spectrum data obtained from one of the inspection apparatuses may be used to characterize structures and/or materials of part of the complete target structure T, prior to calculating a property of the structure using spectrum data obtained from the other metrology apparatus. All these operations may be automated by metrology processing unit 320.

A reflection axis R in FIG. 3 indicates an angle of reflection Or, which is naturally a function of the angle of incidence θi of the illuminating radiation beam 456, relative to an axis N normal to the plane of the substrate W and target T. Radiation beam 456 is at least partially reflected into a zero order beam 458 which is optionally detected by detection system 418, or may be dumped. In principle, asymmetry or other parameters of interest can be measured from (zero order) reflection spectra, but asymmetry information will be stronger in the higher order diffracted beams 460+ and 460− which are diffracted at angles either side of the reflection axis R, as shown. Higher order diffracted beams may be any combination of first, second, third, etc. diffraction orders.

For simplicity, we shall refer simply to the "higher order" or "first order" beams, without signifying any limitation. The relative angles of the different orders will depend in a known manner on the wavelength(s) of the radiation and the spatial period of grating structures present in the target. The angles shown in the drawing are purely for illustration of the principle.

Accordingly, a method of metrology may include using second spectrum data 384 representing higher order diffraction spectra from a periodic structure to measure asymmetry in the structure. The structure may be one of a plurality of biased gratings. As is known from diffraction based overlay at visible wavelengths, the asymmetry can be calculated by comparing the intensity of opposite portions of the diffraction spectrum, for example, by comparing +1 and −1 order diffracted radiation. The detection system 418 in the illustrated example captures both diffracted beams 460+ and 460− simultaneously. Within detection system 418, there may be a single radiation-detecting element for each beam, or there may be an array of detecting elements, such as a 1- or 2-dimensional array of pixels. A single image sensor may extend so as to capture both beams 460+ and 460− on different regions of pixels. In the case of a target having periodicity in the Y direction (into the plane of the drawing), diffracted beams will be directed at similar angles into and out of the page. Detection system can be arranged to capture these diffracted beams also.

Because of the short wavelengths of the illuminating radiation beam, the target can be made of the smallest product features or product-like features, which is not possible with current optical techniques using longer wavelengths. Sensitivity to overlay is expected to be greater than current tools. By combining different types of measurement in the hybrid metrology system of FIG. 2, further improvements in accuracy can be obtained.

In the configuration shown in FIG. 3, the angle of incidence θi of the illuminating radiation is asymmetrical with respect to the normal axis N. The opposite portions of the diffraction spectrum are therefore found symmetrically either side of the reflection axis, R, which is also asymmetrical with respect to the normal axis. Processing of the asymmetrical signals can be adapted either by calibration with known structures or other means, to discriminate between asymmetry of the target and asymmetry of the measurement configuration. A number of methods can be used to correct for this asymmetry of the sensing arrangement. Techniques described, for example, in published patent applications US20080239318 A1, US20110292365 A1 or US20120242970 A1. By rotating the target through 180°, opposite portions of the diffraction spectrum could be detected sequentially with only half of the detection system 418. This may be a useful option, for example, where the diffraction angle of beam 460− would cause a conflict between the position of the detector and the path of illuminating radiation beam 456.

Figure 4:
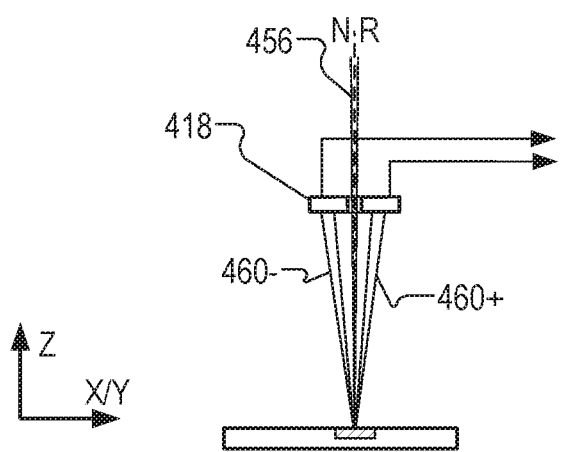
FIG. 4 shows a partial detail of a second embodiment of an inspection apparatus in which the present invention may be applied.

In the alternative configuration illustrated in FIG. 4, the angle of incidence of the illuminating radiation beam 456 is the same as or very close to the normal axis N. The reflection axis R and the direction of the zero order reflected beam 458, therefore, coincide with the normal axis too. The opposite portions of the diffraction spectrum are therefore found symmetrically either side of the normal axis. Detection system 418 in this case extends symmetrically either side of the normal axis and the illuminating radiation beam 456 (and in the Y direction also). Detection system 418, in this case, may comprise separate detector arrays with a space between them for the passage of the illuminating radiation beam 456. Alternatively, detection system 418, in this case, may comprise separate detector arrays with a spec between them for the passage of the illuminating radiation beam 456. Alternatively, detection system 418 may comprise a single 2-dimensional image sensor, with an aperture formed in it to allow passage of the illuminating radiation beam 456 and zero order beam 458. The sensor or sensors are placed where they will capture a far-field scatter pattern (diffraction spectrum) from the interaction of the illuminating radiation and the target.

Referring now to FIG. 5, a composite overlay target is formed on a substrate W by a lithographic process whose performance is being monitored. The composite target comprises four gratings 52 to 55 positioned closely together, only by way of example. The measurement spot S formed by the illumination beam of the metrology apparatus fits entirely within one grating at a time. A radiation spot 51 (e.g., circle) indicates the extent of spot S on the substrate W. In an example dedicated to overlay measurement, gratings 52 to 55 are overlay gratings formed by overlying gratings that are patterned in different layers of the semiconductor device formed on substrate W (as in FIG. 2 (b)). Gratings 52 to 55 may have differently biased overlay offsets in order to facilitate measurement of overlay between the layers in which the different parts of the composite gratings are formed. Gratings 52 to 55 may also differ in their orientation, as shown, so as to diffract incoming radiation in X and Y directions. In one example, gratings 52 and 54 are X-direction gratings with biases of the +d, −d, respectively. This means that grating 52 has its overlying components arranged so that if they were both printed exactly at their nominal locations one of the components would be offset relative to the other by a distance d. Grating 54 has its components arranged so that if perfectly printed there would be an offset of d but in the opposite direction to the first grating and so on. Gratings 53 and 55 are Y-direction gratings with offsets +d and −d respectively.

FIG. 5 (b) shows the diffraction spectrum 518 captured by an image sensor in the detection system 418 of the second inspection apparatus when radiation spot 51 is illuminating grating 52 with features periodic in the X direction. Image sensor in this example has an aperture 520 to allow passage of the illumination radiation beam 456, as described above. Bright spots 560+ and 560− indicate the regions where the first order beams 460− and 460+ of diffracted radiation impinge on the detector surface. By comparing (subtracting) intensity values corresponding to opposite parts of the diffraction spectrum, an asymmetry value Ax for grating 52 can be obtained and used to calculate, for example, overlay in the X direction.

The comparison (subtraction) of intensity values can be performed pixel-by-pixel and averaged over the spectrum. The intensity could alternatively be averaged for identified regions of interest before the comparison is performed. It will be noted that the example spectrum of FIG. 5(b) has multiple bright regions. These are each the result of a single +1 or −1 order diffracted beam 460+ or 460−, but for a different wavelength of radiation included within the illuminating radiation beam 456. In the case of an HHG radiation source, typically multiple harmonic wavelengths will be excited in the gas. It is an option to combine asymmetry values for all the wavelengths together, or to select only certain ones of the bright regions and thereby select only signals of a certain wavelength of wavelengths. It is a matter of implementation, whether the regions of interest are recognized within the spectrum after it has been recorded by the detector, or whether regions of interest are defined in advance.

In addition to seeing regions corresponding to first order diffraction at different wavelengths, the image sensor in practice may also capture multiple diffraction orders for a single wavelength, and/or a combination of multiple diffraction orders for multiple wavelengths.

To obtain an overlay measurement, the above procedure is repeated to obtain a measurement of asymmetry Ax while illuminating the other X-direction grating 54. The diffraction spectrum will look similar to that shown in FIG. 5(b), but with intensity values specific to the grating. The two asymmetry values can be combined with knowledge of the overlay bias values programmed into the gratings, to obtain a value for overlay in the X direction, as a measure of performance of the lithographic process that was used to form the targets.

To measure asymmetry and overlay in the Y direction, the spot S is moved firstly to the grating 53, where its outline is labeled 51'. FIG. 5(c) shows the diffraction spectrum 518' obtained from grating 53. Because the grating 53 is periodic in the y direction, the diffraction spectrum is spread in the Y direction on the image sensor. Intensity values from bright regions 560'+ and 560'− are compared to obtain a measure of asymmetry Ay with respect to the Y direction. By repeating this measurement with the spot S moved to grating 55, a second value of asymmetry Ay can be obtained. Combining the two asymmetry values with knowledge of the overlay bias values applied in the gratings 53 and 55, a value for overlay in Y direction can be obtained as another measure of performance of the lithographic process.

It will be appreciated that, according to the method illustrated in FIG. 5, to obtain measurements in both the X and Y directions takes twice as many illumination and detection steps as are required for a single direction. With reference now to FIG. 6, there will be explained a modification to the second inspection apparatus 400, by which asymmetry in both X and Y directions can be measured simultaneously.

FIG. 6 (a) shows the same set of gratings 52 to 55 that are shown in FIG. 5 (a). However, instead of illuminating gratings 52 and 53 sequentially with the radiation spot 51/51', the inspection apparatus 400 modified in accordance with the present disclosure, is arranged to illuminate the gratings 52 and 53 simultaneously, with two spots 61a and 61b. FIG. 6(b) shows the resulting diffraction spectrum 618 on the image sensor within detection system 418. Now it can be seen that diffraction orders in both the X and Y directions are simultaneously captured. Because the direction of diffraction is different between the two gratings 52 and 53, the bright regions of the diffraction spectra generated by interaction of radiation with the different gratings are spatially separated on the image sensor. Regions 660x+ and 660x− correspond to opposite portions of the diffraction spectrum of the grating 52, while regions 660y+ and 660y− correspond to opposite portions of the diffraction spectrum of the grating 53. The sensor does not need to be an image sensor with a great number of pixels. Provided that the sensor has enough radiation detecting elements and that they are positioned so that they do not mix the X and Y diffraction regions, the asymmetry Ax of the grating 52 in the X direction can be measured using the same illumination and detection step as the asymmetry Ay of the grating 53 in the Y direction. The process can be repeated for the other two gratings 54 and 55, to obtain further asymmetry values, and hence an overlay value in each direction X and Y can be obtained with half the number of illumination and detection steps as in the method of FIG. 5. It will be understood that this method can also be used with any two non-parallel directions, and the orthogonal directions X and Y are cited as a common example only. The method can also be applied with more than two directions, provided the directions are non-parallel with one another.

Figure 7:
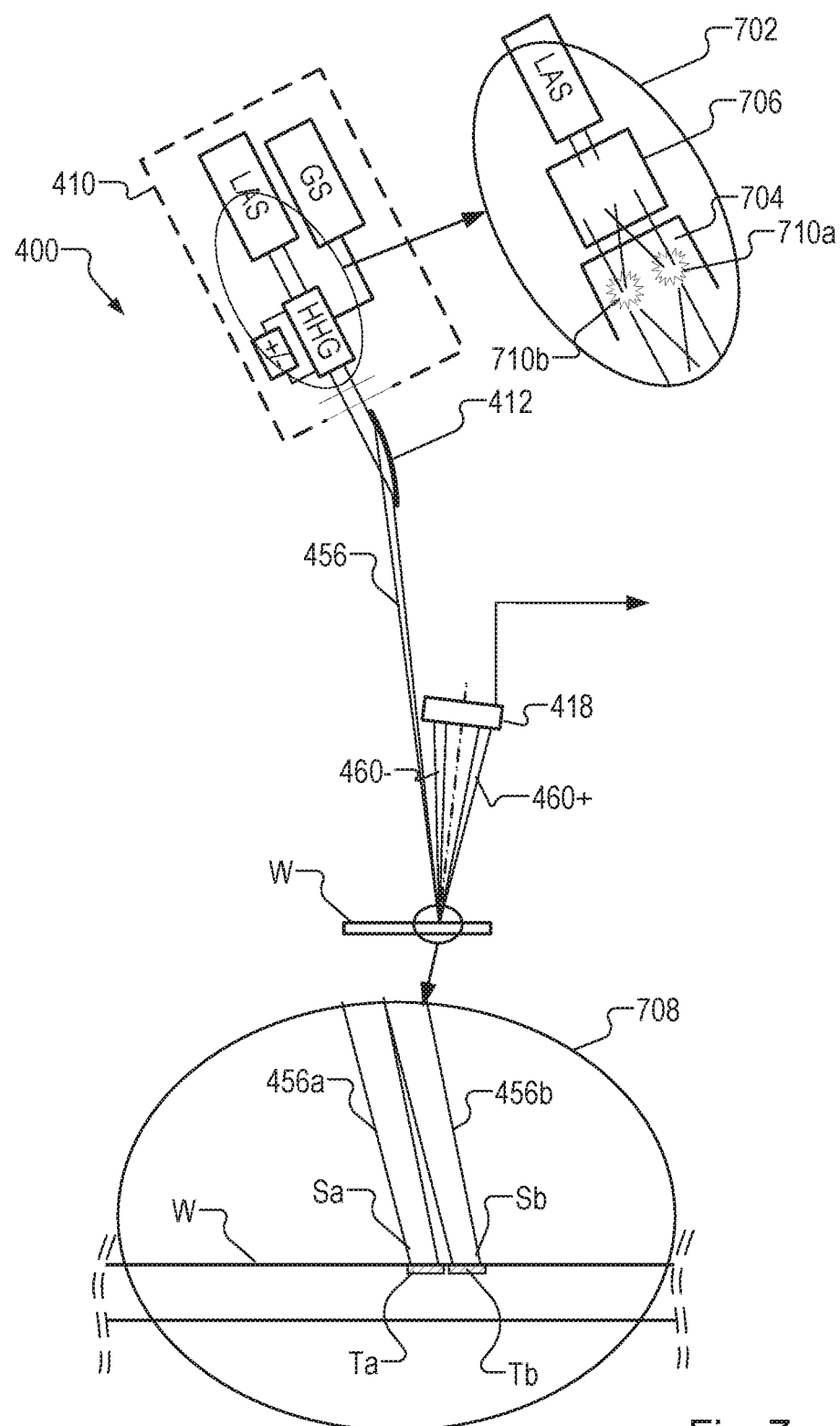
FIG. 7 shows in more detail the simultaneous illumination of two targets by the inspection apparatus of FIG. 3 or 4.

FIG. 7 shows schematically the modification to the radiation source 410, which is applied to achieve the two illumination spots 61a and 61b in the method of FIG. 6. The main part of the drawing, simply reproduces the radiation source 410, the illumination system 412 and the detection system 418 of the second inspection apparatus 400. A first inset detail 702 shows an enlarged detail of the higher harmonic generation space 704 and laser beam delivery system 706. A second inset detail 708 shows an enlarged detail of the target region on the substrate W.

The basic components and principles of operation of the HHG radiation source are as described above with respect to FIG. 3. Like a conventional HHG radiation source, radiation source 410 uses a laser beam delivery system 706 to focus infrared radiation from the pump laser to an excitation location within the gas-filled higher harmonic generation space 704. In the modified radiation source, however, instead of one excitation location, the pump radiation is focused simultaneously on two excitation source locations, labeled 710a and 710b. Each of these locations becomes a source of shorter wavelength radiation having one or (typically) several wavelengths in the SXR waveband 1-100 nm.

Illumination system 412 images the HHG source locations 710a and 710b onto the substrate surface to become the focused spot of radiation on the target T. Provided the source locations are chosen so that they both are focused in the same plane relative to the substrate, then a portion 456a of the illuminating radiation beam 456 obtained from source location 710a will be focused into a first spot Sa, and simultaneously a second portion 456b of the illuminating radiation beam 456 will be focused into a second spot Sb at a slight distance away. The spacing of these spots in the plane of the targets (controlled by the spacing of the excitation locations and the magnification of the illumination system 412) can be matched to the spacing of two targets Ta and Tb as shown in the inset detail 780.

By appropriate adaptation of the laser beam delivery system, characteristics of the radiation from the different source locations can be made different, if desired. For example, the polarization of each source can be made different from the other. In more general terms any characteristic of the radiation can be optimized to suit the different diffraction directions.

Figure 8:
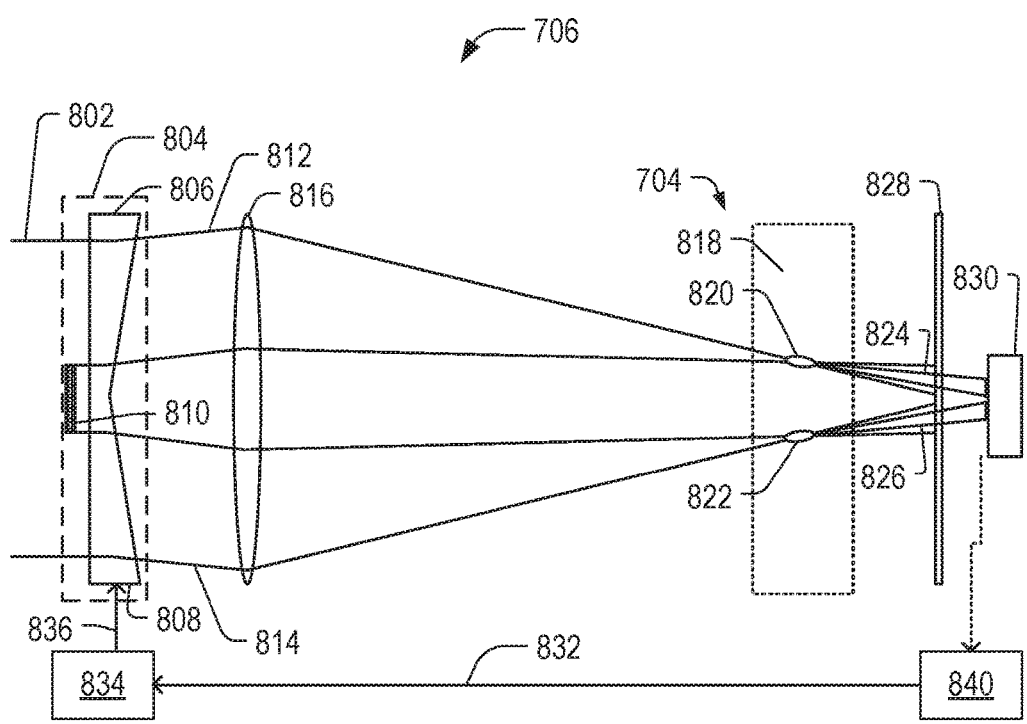
FIG. 8 illustrates in more detail an example arrangement for generating the radiation in the inspection apparatus of FIG. 3 or 4.

FIG. 8 illustrates in more detail one example of the laser radiation delivery system. A laser radiation source (not shown) emits radiation beam 802 with a particular wavelength. In the present example, the radiation source is a femtosecond laser emitting illuminating radiation having an infrared wavelength. The radiation propagates to a first optical element 804, which comprises an optical wedge, which comprises a first optical wedge portion 806, a second optical wedge portion 808 and a stop 810. The stop is positioned so that it blocks the central portion of the radiation beam 802, thereby splitting the radiation beam into first radiation 812 and second radiation 814.

The first and second radiation propagate through a gas 818 in higher harmonic generation space 704. The first optical wedge portion 806 and lens 816 cooperate to focus the first radiation 812 into a first spot 820 inside the gas.

Similarly, second optical wedge portion 808 and lens 816 cooperate to focus the second radiation 814 into a second spot 822 inside the gas jet.

The first spot 820 defines the first excitation location 710*a* in the example of FIG. 7, and the second spot 822 defines the second excitation location 710*b*. The first radiation and the second radiation interact with the gas at each excitation location to provide first illuminating radiation 824 and second illuminating radiation 826. The illuminating radiation passes through an optical element 828 (a filter that suppresses unwanted radiation wavelengths. In the present example, the optical element is an infra-red suppressing filter.

The illuminating radiation (via illumination system 412, not shown) illuminates a target structure provided on a substrate 830. As illustrated in FIG. 7, the target structure comprises a first target and a second target that are spatially separated in the plane of the substrate. The first illuminating radiation illuminates the first target Ta and the second illuminating radiation illuminates the second target Tb. The first illuminating radiation and second illuminating radiation are scattered by the first target and the second target respectively. The scattered radiation (not shown) is detected by a detection system (also not shown) and processed by a processing unit to obtain measurements of the two targets simultaneously.

The processing unit can then be used to control the positioning of one or both of the first or second optical wedges 806, 808 in order to control the relative spatial separation of the first and second illuminating radiation.

The radiation scattered radiation by the targets may be delivered to the detector of the inspection apparatus, which may be the same as the image sensor used to capture the diffraction spectra, or a different detector. The processing unit 840 processes the detected scattered radiation and, based on the processing results, may send correction data 832 to a correction unit 834. The correction unit comprises one or more actuating elements that are connected to one or more of the optical components of the illumination system. In the present example, the correction unit comprises an actuator 836 connected to the second optical wedge portion 808. Based on the correction data, the correction unit activates the actuator to adjust the radiation delivery system as necessary.

It will be appreciated that the components of the laser radiation delivery system shown in FIG. 8 are exemplary only and that the system may comprise additional or alternative components.

While the above examples refer to radiation source arrangements using HHG for generating SXR radiation at desired source locations, x-ray and/or EUV radiation can also be generated using an inverse Compton scattering (ICS) source. More detail of this type of source arrangement is provided in pending international patent application PCT/EP2016/068479 mentioned in the introduction. The content of that application is hereby incorporated by reference. Briefly, in an ICS radiation source, a high energy electron beam interacts with a laser beam in a cavity to generate output radiation at x-ray or longer wavelengths. Using the inverse Compton scattering source, X-ray, EUV, UV and VIS radiation can be generated with high brightness and rapid frequency switching. To generate radiation at two source locations in the same radiation generation space, laser radiation can be focused at two locations in the same electron beam, or in separate electron beams. The first and/or second radiation may have a wavelength in the EUV range of 0.1 nm to 125 nm. Using the same source and controlling an electron energy, the structure may be irradiated multiple times with different wavelengths within the EUV range, and/or with shorter (x-ray) wavelengths and/or with longer (UV, visible) wavelengths. By rapid switching of electron energy in the inverse Compton scattering source, irradiation at different wavelengths can be performed several times per second.

Using modern laser-pumped sources such as the HHG and ICS types mentioned above, high power can be provided in one or more desired wavelengths, compared with conventional sources. Adequate penetration into the stack can thus be obtained, even with a single wavelength in the EUV radiation. Of course, the second radiation may be longer in wavelengths than EUV radiation. Penetration and contrast may be increased by moving to longer wavelengths, while spatial resolution may be lost as a compromise. Using the principles disclosed herein and the sources and optical systems described, the skilled person has a full range of options to choose from in designing an effective inspection apparatus for simultaneous measurement of two targets.

Like the optical scatterometer used in today's production facilities, the inspection apparatus 400 can be used to measure structures within the resist material treated within the litho cell (After Develop Inspection or ADI), and/or to measure structures after they have been formed in harder material (After Etch Inspection or AEI). For example, substrates may be inspected using metrology apparatus 400 after they have been processed by the developing apparatus 212, etching apparatus 222, annealing apparatus 224 and/or other apparatus 226.

In embodiments of the hybrid metrology system 200 according to the present disclosure, it is proposed to use SXR/EUV wavelengths for metrology in at least one of the inspection apparatuses, for the measurement of asymmetry of target structures such as overlay gratings. In another part of the hybrid metrology system, other types of measurement, for example, spectroscopic SXR/reflectometry, is employed as part of the CD-metrology solution for future technological nodes. In the published patent application number US 20160282282 A1, mentioned above, it is demonstrated that SXR reflectometry offers benefits of high sensitivity, being robust against process variations and being selective for a parameter of interest. As illustrated in FIG. 2, signals obtained from the reflectometry at grazing incidence can also be combined with asymmetry measurements made at normal or near-normal incidence, to improve the accuracy of asymmetry-based measurements. For example, an overlay measurement can be made more robust against process variations in the top or bottom grating and/or in layers in between.

Figure 9A:
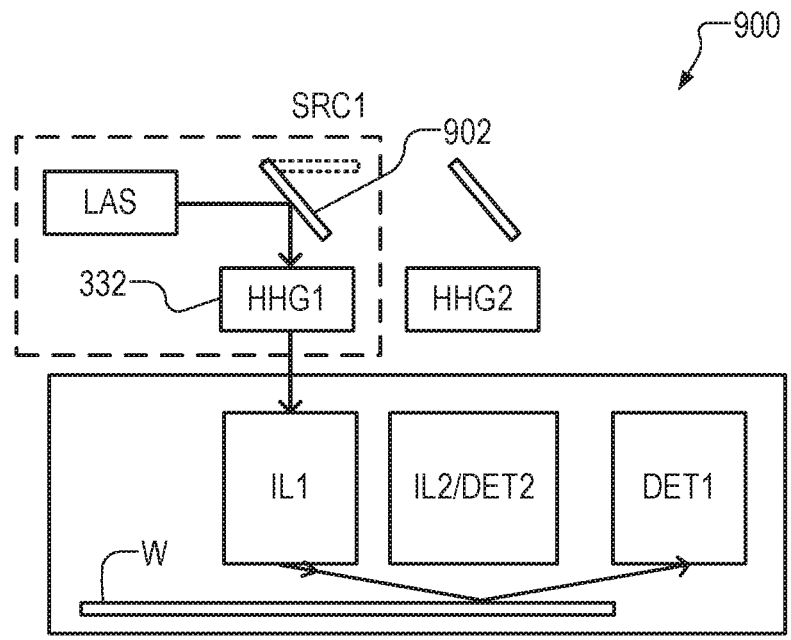
FIGS. 9(a)-9(b) illustrate schematically the sharing of a drive laser in a hybrid metrology apparatus according to further embodiments of the present invention.
Figure 9B:
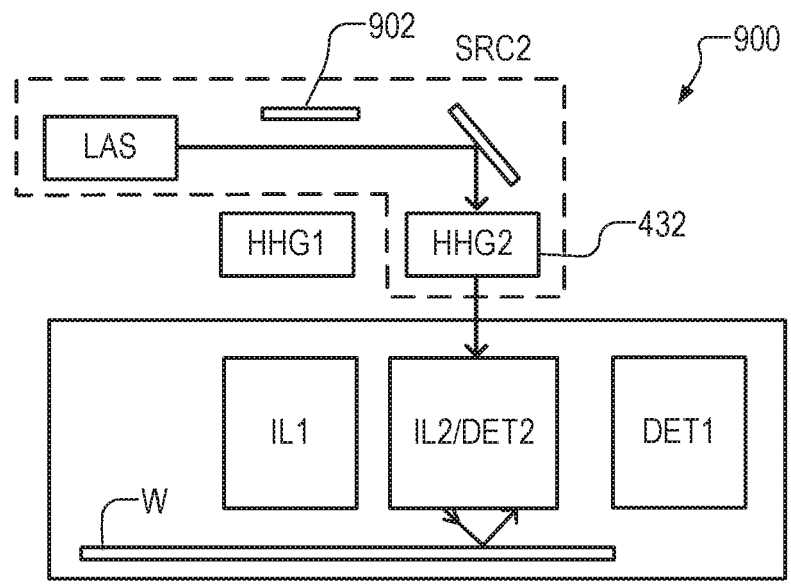

FIG. 9 illustrates an example of a hybrid metrology system 900 in which part of a first radiation source is shared with a second radiation source. It will be appreciated that provision of multiple radiation sources within a single hybrid metrology system may be challenging in terms of cost and physical space. Particularly for those modern sources that provide high brightness and/or control of wavelengths, a pump laser is provided. The pump laser may be designed to generate pulses in the femtosecond time range. An example of a radiation source using a pump laser is the higher harmonic generation (HHG) source illustrated in FIGS. 3-8. Another example is a supercontinuum source, used to provide broadband radiation in known scatterometers.

In FIG. 9 we see the hybrid metrology system in two modes of operation (a) and (b). Within a main body of the system, a first illumination system IL1 and a first detection system DET1 form a first inspection apparatus, which may be an EUV spectroscopic reflectometer, which may be the first inspection apparatus 302 as illustrated in FIG. 3. Between these components, a second illumination system IL2 and second detection system DET2 are provided to form a second inspection apparatus, which may be, for example, the second inspection apparatus 400. In FIG. 9 (*a*), the first inspection apparatus is operating using an HHG source. A movable mirror 902 is positioned to direct pump radiation from pump laser LAS into a first HHG cell (332). SXR radiation is generated in the HHG cell so as described above, and then into the first illumination system ILL In FIG. 9(*b*), the second inspection apparatus is operating using an HHG source to generate SXR radiation at two or more source locations in a second HHG cell (432), in the manner described above. Movable mirror 902 is moved to a second position so that radiation from pump laser LAS enters the second HHG cell. This generates first and second radiation to be supplied to the second illumination system IL2, to illuminate first and second targets Ta and Tb, as described above.

Figure 10:
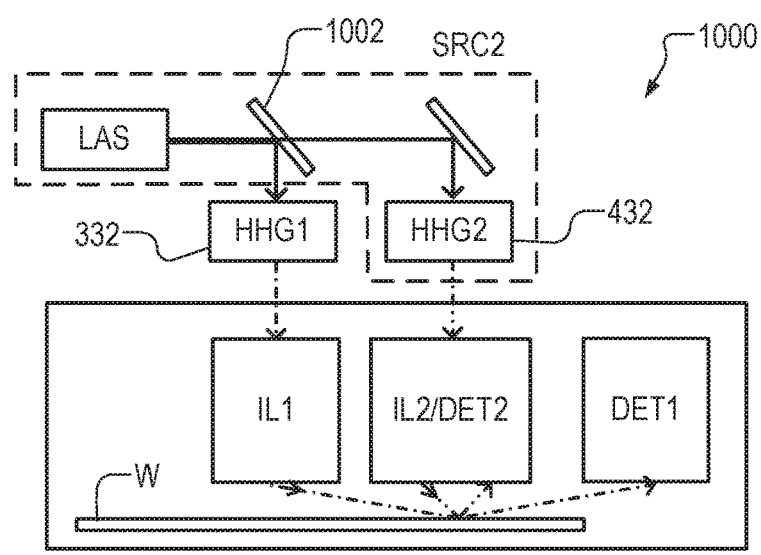
FIG. 10 illustrates schematically the sharing of a drive laser and simultaneous operation of different inspection apparatuses in a hybrid metrology apparatus according to a further embodiment of the present invention.

FIG. 10 illustrates another hybrid metrology system 1000 which is the same as shown in FIG. 9, except the laser radiation is split into two paths by a beam splitter 1002 instead of being switched by movable mirror 902. In this way, the first and second inspection apparatuses can operate simultaneously. Provided the radiation after interaction with the target is scattered in different directions, the separate detection systems DEt1 an DET2 can operate simultaneously. If there is a risk of cross-talk between the radiation of the two inspection apparatuses, this can be avoided by using different wavelengths of radiation in the two inspection apparatuses. The wavelength can be changed by changing the choice of gas and/or other factors in the respective HHG cells 332, 432.

Further modifications of the laser radiation delivery system and other components of the HHG radiation source can be included, which are not detailed herein. Some of these modifications are disclosed, for example, in European patent application number 16198346.5 dated Nov. 11, 2016, not been published at the priority date of the present application. Other modifications are disclosed in U.S. patent application Ser. No. 15/388,463 and international patent application PCT/EP2016/080103, both claiming priority from European patent application no. 15202301.6 dated Dec. 23, 2015 also not yet been published at the priority date of the present application. The contents of both of these applications are incorporated herein by reference, and the techniques described therein can be used in combination with the techniques of the present disclosure. As also mentioned, inverse Compton scattering (ICS) can be used instead of HHG as a mechanism to generate the desired SXR radiation from laser radiation of a lower wavelength. The same principles of generating the desired radiation at two source locations can be applied by appropriate laser beam delivery arrangements in the path of an electron beam as a radiation conversion medium, as in the case of a gaseous conversion medium in HHG.

While the examples above show two distinct spots of radiation being applied to the first and second targets, a measurement of asymmetry in two targets could be obtained by filling the two targets with a single spot. In such an embodiment, the first and second radiation would be portions of a single radiation beam. In such an embodiment, obviously the facility to generate first and second radiation with different characteristics would be limited or lost entirely, but the source design and operation would be simplified. Also, there may be noise in the diffraction signals, caused by scattering at the edges of the target structures or the interface between the target structures.

While the present disclosure presents SXR radiation between 1-100 nm as an example of particular interest for current technological development, shorter wavelengths in the harder x-ray range, less than 1 nm and potentially less than 0.1 nm. While inspection by reflection of radiation is described by way of example, the principles of the present disclosure may also be applied in transmissive arrangements, particularly where shorter x-ray radiation can penetrate through the whole substrate.

Figure 11:
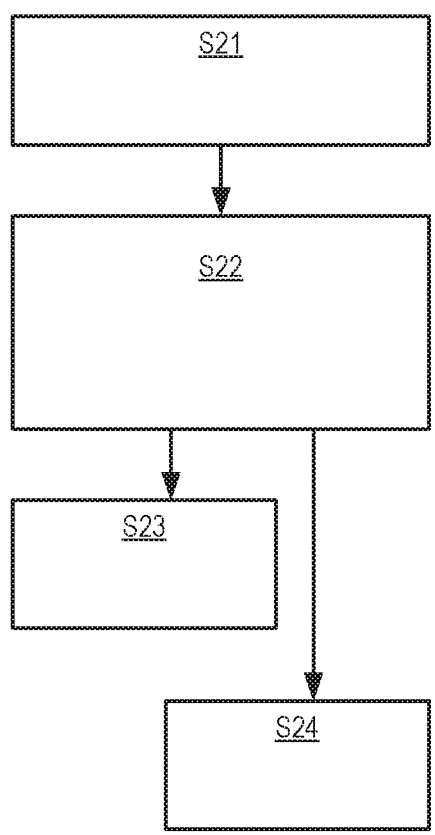
FIG. 11 is a flow chart illustrating a method of controlling performance of a metrology method and/or of a lithographic manufacturing process using measurements made by the hybrid metrology system of FIG. 1.

FIG. 11 illustrates the application an inspection apparatus such as inspection apparatus 400, in the control of a lithographic manufacturing system of the type illustrated in FIG. 1. The steps will be listed here, and then explained in more detail:

S21: Process wafer to produce structures on the substrate
S22: Measure CD and/or other parameter across the substrate
S23: Update metrology recipe
S24: Update lithography and/or process recipe At step S21, structures are produced across a substrate using the lithographic manufacturing system. At S22, the metrology apparatus 140 and optionally other metrology apparatus and information sources are used to measure a property of the structures across the substrate. In accordance with the principles of the present disclosure, set forth above, properties of two or more targets are measured per illumination-detection step, with regard to first and second directions. By measuring multiple biased targets in this way, a performance parameter such as overlay is measured at one or more locations across the substrate.

At step S23, optionally, metrology recipes and calibrations of the metrology apparatus are updated in light of the measurement results obtained. Referring again to the discussion of FIGS. 5 and 6 above, a metrology recipe might specify which portions of the diffraction spectra to compare for the most reliable asymmetry measurement. The recipe may specify settings of the laser radiation delivery system also, for example, to control polarization of the SXR radiation.

At step S24, measurements of overlay or other performance parameters are compared with desired values, and used to update settings of the lithographic apparatus and/or other apparatus within the lithographic manufacturing system. By providing an inspection apparatus that can measure twice as many targets per illumination-detection step, more measurements can be obtained for a given measurement overhead. This, in turn, can lead to better performance when the results of measurements are applied in further measurements and in further control of the lithographic apparatus.

While embodiments of the metrology target described herein have mostly been described in the terms of overlay measurement, similar techniques can be applied to measure one or more additional or alternative patterning process parameters. For example, appropriately designed metrology targets may be used to measure exposure dose variation, measure exposure focus/defocus, measure CD, etc., all based on asymmetry difference between pairs of biased gratings.

While the target structures described above are metrology targets specifically designed and formed for the purposes of measurement, in other embodiments, properties may be measured on targets which are functional parts of devices formed on the substrate. Many devices have regular, periodic structures akin to a grating. The term "target", "grating"

or "periodic structure" of a target as used herein does not require that the applicable structure has been provided specifically for the measurement being performed. Further, pitch P of the metrology target is close to the resolution limit of the optical system of the measurement tool, but may be much larger than the dimension of typical product features made by a patterning process in the target portions C. In practice the features and/or spaces of the gratings may be made to include smaller structures similar in dimension to the product features.

In association with the physical structures of the targets as realized on substrates and patterning devices, an embodiment may include a computer program containing one or more sequences of machine-readable instructions and/or functional data describing the target design, describing a method of designing a target for a substrate, describing a method of producing a target on a substrate, describing a method of measuring a target on a substrate and/or describing a method of analyzing a measurement to obtain information about a patterning process. This computer program may be executed, for example, within metrology processing unit MPU in the apparatus of FIGS. 3 to 9 and/or the control unit LACU of FIG. 2. There may also be provided a data storage medium (e.g., semiconductor memory, magnetic or optical disk) having such a computer program stored therein. Where an existing inspection apparatus, for example, of the type shown in FIG. 3, is already in production and/or in use, an embodiment can be implemented by the provision of an updated computer program product for causing a processor to perform one or more of the methods described herein (e.g., to recognize different parts of the diffraction spectrum captured in the detection system 418, to calculate overlay error as described herein). The program may optionally be arranged to control the optical system, substrate support and the like to perform a method of measuring a parameter of the patterning process on a suitable plurality of targets (e.g., to measure asymmetry on a suitable plurality of targets and/or to determine overlay error). The program can update a parameter of the patterning process and/or of the metrology recipe, for measurement of further substrates. The program may be arranged to control (directly or indirectly) the lithographic apparatus for the patterning and processing of further substrates.

Further embodiments are disclosed in the subsequent numbered clauses:

1. An inspection apparatus comprising an illumination system and a detection system, wherein the illumination system includes a source arrangement for generating first radiation at a first source location in a radiation generation space and for simultaneously generating second radiation at a second source location in the same radiation generation space, the first radiation and the second radiation including wavelengths less than 100 nm, wherein an optical system of the illumination system is arranged to focus radiation from both the first source location and the second source location so as to illuminate a first target location with a spot of said first radiation while simultaneously illuminating a second target location with a spot of said second radiation, and wherein the detection system is arranged to detect, at one or more first detection locations, portions of said first radiation that have been diffracted in a first direction by a first target structure at the first target location and simultaneously to detect, at one or more second detection locations, portions of said second radiation that have been diffracted in a second direction by features of a second target structure positioned at the second target location.

2. An inspection apparatus as defined in clause 1 further comprising a processing arrangement for calculating a first asymmetry-related property of the first target based on the portions of the first radiation detected at said first detected locations and for calculating a second asymmetry-related property of the second target based on the portions of the second detected at said second detection locations.

3. An inspection apparatus as defined in clause 2 wherein said processing arrangement is further arranged to calculate a first performance parameter of a lithographic process based on the first asymmetry-related property of one or more first targets and to calculate a second performance parameter of the lithographic process based on the second asymmetry-related property of one or more second targets.

4. An inspection apparatus as defined in clause 3 wherein said first performance parameter represents overlay performance in said first direction and said second performance parameter represents overlay performance in said second direction.

5. An inspection apparatus as defined in any preceding clause wherein said detection system includes a first plurality of radiation-sensitive detector elements for detecting radiation at different ones of said first detection locations and having a second plurality of radiation sensitive detector elements for detecting radiation at different ones of said second detection locations.

6. An inspection apparatus as defined in clause 5 wherein at least some of said first plurality of detector elements and some of said second plurality of detector elements are provided at different locations on a common multi-element detector.

7. An inspection apparatus as defined in any preceding clause wherein said illumination system is operable to illuminate the first target and second target with radiation at an angle normal to a target plane containing the first and second targets, the first detection locations and second detection locations being arrayed symmetrically about an axis normal to the target plane.

8. An inspection apparatus as defined in any of clauses 1 to 6 wherein said illumination system is operable to illuminate the first target and second target with radiation at a non-normal incidence angle relative to a target plane containing the first and second targets, the first detection locations and second detection locations being arrayed asymmetrically about an axis of reflection defined by the incidence angle and the target plane.

9. An inspection apparatus as defined in any preceding clause wherein the source arrangement is operable to focus first laser radiation at said first source location and to focus second laser radiation at said second source location, for causing generation of said first radiation and second radiation respectively at wavelengths different to the wavelength of the first and second laser radiation.

10. An inspection apparatus as defined in clause 9 wherein said source arrangement is further operable to deliver a gaseous medium to said radiation generating space such that said first radiation and second radiation are generated by higher harmonic generation from their respective first and second laser radiation.

11. An inspection apparatus as defined in clause 9 wherein said source arrangement is further operable to deliver an electron beam to said radiation generating space such that said first radiation and second radiation are generated from their respective first and second laser radiation by inverse Compton scattering.

12. A method of inspecting structures that have been formed on a substrate by a lithographic process, the method comprising:

illuminating a first target with first radiation and simultaneously illuminating a second target with second radiation, the first radiation and the second radiation including wavelengths less than 100 nm;

detecting, at one or more first detection locations, portions of said first radiation that have been diffracted in a first direction by features of the first target; and detecting, at one or more second detection locations, portions of said second radiation that have been diffracted in a second direction by features of the second target.

13. A method as defined in clause 12 further comprising calculating a first asymmetry-related property of the first target based on the portions of the first radiation detected at said first detected locations and calculating a second asymmetry-related property of the second target based on the portions of the second targets detected at said second detection locations.

14. A method as defined in clause 13 further comprising calculating a first performance parameter of the lithographic process based on the first asymmetry-related property of one or more first targets and calculating a second performance parameter of the lithographic process based on the second asymmetry-related property of one or more second targets.

15. A method as defined in clause 14 wherein said first performance parameter represents overlay performance in said first direction and said second performance parameter represents overlay performance in said second direction.

16. A method as defined in any of clauses 12 to 15 wherein a first plurality of radiation-sensitive detector elements are used for detecting diffracted radiation at different ones of said first detection locations and a second plurality of radiation sensitive detector elements are used for detecting diffracted radiation at different ones of said second detection locations.

17. A method as defined in clause 16 wherein at least some of said first plurality of detector elements and some of said second plurality of detector elements are provided at different locations on a common multi-element detector.

18. A method as defined in any of clauses 12 to 17 wherein the first target and second target are illuminated respectively with said first radiation and said second radiation at an angle normal to a target plane containing the first and second targets, the first detection locations and second detection locations being arrayed symmetrically about an axis normal to the target plane.

19. A method as defined in any of clauses 12 to 17 wherein the first target and second target are illuminated respectively with said first radiation and said second radiation at a non-normal incidence angle relative to a target plane containing the first and second targets, the first detection locations and second detection locations being arrayed asymmetrically about an axis of reflection defined by the incidence angle and the target plane.

20. A method as defined in any of clauses 12 to 19 wherein the first target is illuminated with a spot of first radiation underfilling the first target and simultaneously the second target is illuminated with a spot of second radiation underfilling the second target 21. A method as defined in clause 20 wherein said first radiation is generated at a first source location in a radiation generation space and simultaneously said second radiation is generated at a second source location in the same radiation generation space, wherein a common optical system is used to focus radiation from both the first source location and the second source location so as to generate said spot of first radiation and said spot of said second radiation.

22. A method as defined in clause 20 or 21 wherein the said first radiation is generated at said first source location source by focusing first laser radiation at said first source location and said second radiation is generated at said second source location by focusing second laser radiation at said second source location, for causing generation of said first radiation and second radiation respectively at wavelengths different to the wavelength of the first and second laser radiation.

23. A method as defined in clause 22 wherein said first radiation and second radiation are generated by delivering a gaseous medium to the radiation generation space to cause higher harmonic generation from the respective first and second laser radiation.

24. A method as defined in clause 23 wherein said first radiation and second radiation are generated by delivering an electron beam to said radiation generating space such that said first radiation and second radiation are generated from their respective first and second laser radiation by inverse Compton scattering.

25. A method of manufacturing devices, the method including a lithographic process step, wherein, before or after performing said lithographic process step, measurements are obtained of first and second targets on a substrate by a method as defined in any of clauses 12 to 25 and wherein the obtained measurements are used to adjust parameters of the lithographic process step for the processing of the substrate and/or further substrates.

26. A computer program product comprising machine-readable instructions for causing a processor to implement the processing arrangement of an inspection apparatus according to any of clauses 2 to 4.

Although specific reference may have been made above to the use of embodiments in the context of optical lithography, it will be appreciated that embodiments of the invention may be used in other applications, for example, imprint lithography, and where the context allows, is not limited to optical lithography. In imprint lithography, a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The foregoing description of the specific embodiments reveals the general nature of embodiments of the invention such that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. An inspection apparatus comprising:
    an illumination system; and
    a detection system,
    wherein the illumination system includes a source arrangement configured to generate first radiation at a first source location in a radiation generation space and configured to simultaneously generate second radiation at a second source location in the same radiation generation space, the first radiation and the second radiation including wavelengths less than 100 nm,
    wherein an optical system of the illumination system is arranged to focus radiation from both the first source location and the second source location so as to illuminate a first target location with a spot of the first radiation while simultaneously illuminating a second target location with a spot of the second radiation, and
    wherein the detection system is arranged to detect, at one or more first detection locations, portions of the first radiation that have been diffracted in a first direction by a first target structure at the first target location and arranged to simultaneously detect, at one or more second detection locations, portions of the second radiation that have been diffracted in a second direction by features of a second target structure positioned at the second target location.

2. The inspection apparatus of claim 1, further comprising:
    a processing arrangement configured to calculate a first asymmetry-related property of the first target based on the portions of the first radiation detected at the first detected locations and to calculate a second asymmetry-related property of the second target based on the portions of the second detected at the second detection locations.

3. The inspection apparatus of claim 2, wherein the processing arrangement is further arranged to calculate a first performance parameter of a lithographic process based on the first asymmetry-related property of one or more first targets and to calculate a second performance parameter of the lithographic process based on the second asymmetry-related property of one or more second targets.

4. The inspection apparatus of claim 3, wherein the first performance parameter represents overlay performance in the first direction and the second performance parameter represents overlay performance in the second direction.

5. The inspection apparatus of claim 1, wherein the detection system comprises:
    a first plurality of radiation-sensitive detector elements configured to detect radiation at different ones of the first detection locations; and
    a second plurality of radiation sensitive detector elements configured to detect radiation at different ones of the second detection locations.

6. The inspection apparatus of claim 5, wherein at least some of the first plurality of detector elements and some of the second plurality of detector elements are provided at different locations on a common multi-element detector.

7. The inspection apparatus of claim 1, wherein the illumination system is operable to illuminate the first target and second target with radiation at an angle normal to a target plane containing the first and second targets, the first detection locations and second detection locations being arrayed symmetrically about an axis normal to the target plane.

8. The inspection apparatus of claim 1, wherein the illumination system is operable to illuminate the first target and second target with radiation at a non-normal incidence angle relative to a target plane containing the first and second targets, the first detection locations and second detection locations being arrayed asymmetrically about an axis of reflection defined by the incidence angle and the target plane.

9. The inspection apparatus of claim 1, wherein the source arrangement is operable to focus first laser radiation at the first source location and to focus second laser radiation at the second source location, to cause generation of the first radiation and second radiation respectively at wavelengths different to the wavelength of the first and second laser radiation.

10. The inspection apparatus of claim 9, wherein the source arrangement is further operable to deliver a gaseous medium to the radiation generating space, such that the first radiation and second radiation are generated by higher harmonic generation from their respective first and second laser radiation.

11. The inspection apparatus of claim 9, wherein the source arrangement is further operable to deliver an electron beam to the radiation generating space such that the first radiation and second radiation are generated from their respective first and second laser radiation by inverse Compton scattering.

12. A method of inspecting structures that have been formed on a substrate by a lithographic process, the method comprising:
    illuminating a first target with first radiation;
    substantially simultaneously illuminating a second target with second radiation, the first radiation and the second radiation including wavelengths less than 100 nm;
    detecting, at one or more first detection locations, portions of the first radiation that have been diffracted in a first direction by features of the first target; and
    detecting, at one or more second detection locations, portions of the second radiation that have been diffracted in a second direction by features of the second target.

13. The method of claim 12, further comprising:
    calculating a first asymmetry-related property of the first target based on the portions of the first radiation detected at the first detected locations; and
    calculating a second asymmetry-related property of the second target based on the portions of the second targets detected at the second detection locations.

14. The method of claim 13, further comprising:
    calculating a first performance parameter of the lithographic process based on the first asymmetry-related property of one or more first targets; and
    calculating a second performance parameter of the lithographic process based on the second asymmetry-related property of one or more second targets.

15. The method of claim 14, wherein the first performance parameter represents overlay performance in the first direction and the second performance parameter represents overlay performance in the second direction.

16. The method of claim 12, further comprising:
    using a first plurality of radiation-sensitive detector elements for detecting diffracted radiation at different ones of the first detection locations; and using a second plurality of radiation sensitive detector elements for detecting diffracted radiation at different ones of the second detection locations.

17. The method of claim 12, further comprising:
illuminating the first target with a spot of first radiation underfilling the first target; and
substantially simultaneously illuminating the second target with a spot of second radiation underfilling the second target.

18. The method of claim 17, further comprising:
generating the first radiation at a first source location in a radiation generation space;
substantially simultaneously generating the second radiation at a second source location in the same radiation generation space; and
focusing radiation from both the first source location and the second source location using a common optical system so as to generate the spot of first radiation and the spot of the second radiation.

19. A method of manufacturing devices comprising:
a lithographic process step, wherein, before or after performing the lithographic process step, measurements are obtained of first and second targets on a substrate by a method comprising,
illuminating a first target with first radiation,
substantially simultaneously illuminating a second target with second radiation, the first radiation and the second radiation including wavelengths less than 100 nm,
detecting, at one or more first detection locations, portions of the first radiation that have been diffracted in a first direction by features of the first target, and
detecting, at one or more second detection locations, portions of the second radiation that have been diffracted in a second direction by features of the second target; and
using the obtained measurements to adjust parameters of the lithographic process step for the processing of the substrate and/or further substrates.

20. A non-transitory computer program product comprising machine-readable instructions for causing a processor to implement the processing arrangement of an inspection apparatus to perform operations comprising:
illuminating a first target with first radiation;
substantially simultaneously illuminating a second target with second radiation, the first radiation and the second radiation including wavelengths less than 100 nm;
detecting, at one or more first detection locations, portions of the first radiation that have been diffracted in a first direction by features of the first target; and
detecting, at one or more second detection locations, portions of the second radiation that have been diffracted in a second direction by features of the second target.

* * * * *